United States Patent [19]

Reiter

[11] Plant 4,485

[45] Nov. 20, 1979

[54] RASPBERRY PLANT

[76] Inventor: J. Miles Reiter, 315 Vista Dr., La Selva Beach, Calif. 95076

[21] Appl. No.: 904,150

[22] Filed: May 9, 1978

[51] Int. Cl.[2] ..... A01H 5/00

[52] U.S. Cl. ..... Plt./46

[58] Field of Search ..... Plt./46

[56] References Cited

PUBLICATIONS

Anon. (1977), Dean Foster Nurseries 1977 Catalog and Price List, Publisher Unknown, published for Dean Foster Nurseries, Hartford, Mich. 49057, pp. 32 and 34.

*Primary Examiner*—Robert E. Bagwill
*Assistant Examiner*—James R. Feyrer
*Attorney, Agent, or Firm*—Townsend and Townsend

[57] ABSTRACT

A new and distinct red raspberry plant particularly characterized by its everbearing fruiting habit by which fruit is borne on primocanes during the first year after planting and on primocanes and floricanes during subsequent years. The plant is also distinguished by its thornlessness and its tolerance to the Pytophthera root rot species. The plant displays exceptional early cropping in spring and fall with production starting about the first of May peaking during the end of May and the first part of June. Fall production peaks from early August until mid-September. The plant is one of high yield and produces continuously from May until December. Cropping is about one month earlier than Willamette and yields are greater. A marked characteristic of the plant is the purple coloration of immature leaves along the edge and on the ridges of the corrugation when exposed to the sun. The purpling tends toward violet, diminishes in area and ultimately disappears as leaflets mature.

3 Drawing Figures

The present invention or discovery relates to a new and distinct variety of red raspberry which was developed from a raspberry breeding and experimentation program begun about 1937 in the Santa Clara Valley by my father, Joseph M. Reiter, berry grower, and Earl V. Goldsmith, plant hybridizer, both now deceased. Breeding ceased in 1953 and the testing and experimentation was abandoned a few years later.

Some of the test varieties were maintained, however, in a succession of very small holding plots. In spring of 1968, the holding plots which were mixed with a number of experimental varieties were sorted out as to variety and the process of eliminating a number of soil borne diseases was commenced. This process extended over a period of years and in 1973, observations disclosed certain desirable and distinct characteristics of the present variety which was asexually reproduced and a testing program established in Watsonville under my supervision.

The accompanying drawings show specimens of the variety with fruit and foliage in different stages of development. They were taken on about July 20, 1977 when the variety was past its peak of production. Grid lines are 5 cm. (approximately 2.5 in.) apart.

FIG. 1 of the accompanying drawing illustrates plant parts of the new variety typical in size and shape, particularly showing the shape of the torus and the development of the fruit from the green to ripe berries. Also shown is the irregularity of the berry and the uneven ripening process from white to red.

Figure 1:
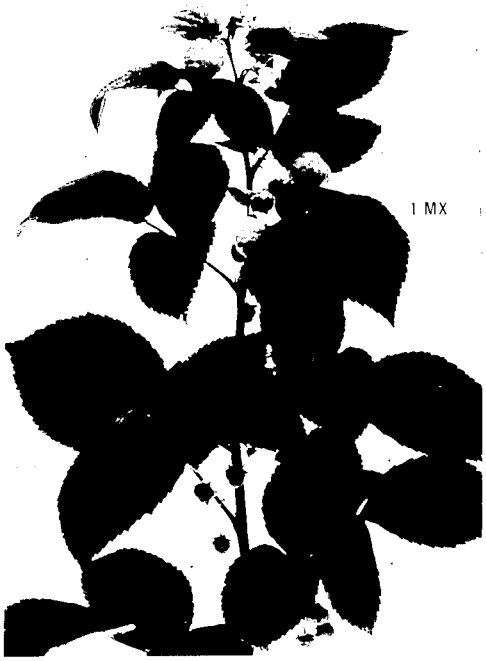
Figure 2:
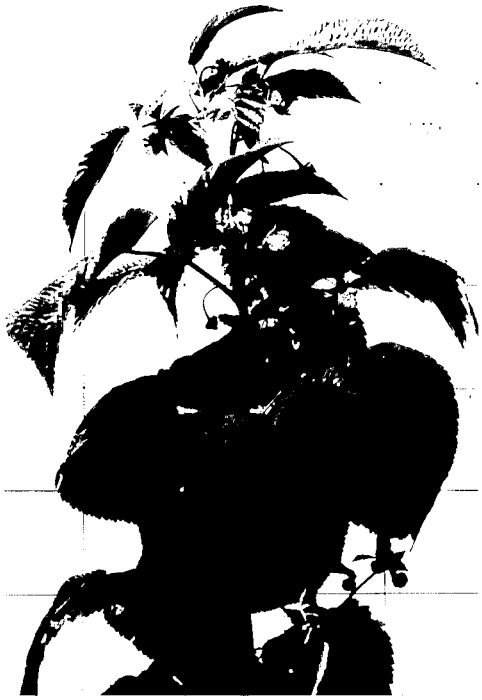
FIG. 2 illustrates the fruit in its transition from bud to green berry and also shows the characteristic purpling of the stem and sepals. The leaf is generally flat and pointed at the end.
Figure 3:
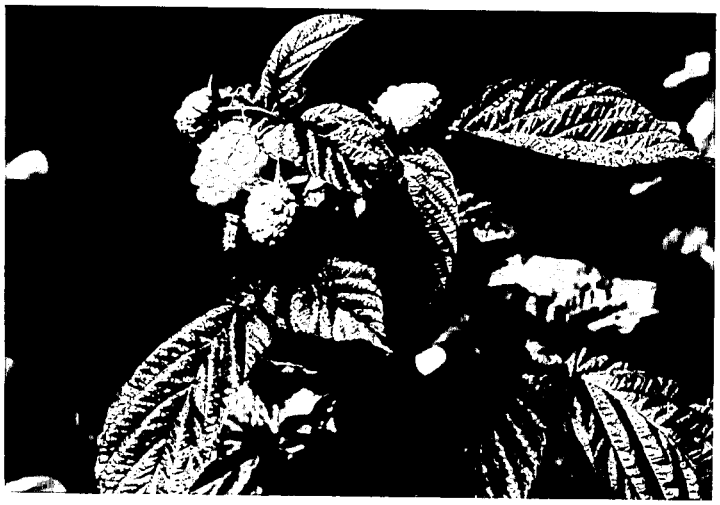
FIG. 3 illustrates the drupelets and shows the prominent median depression manifested by immature fruit.
Figure 4:
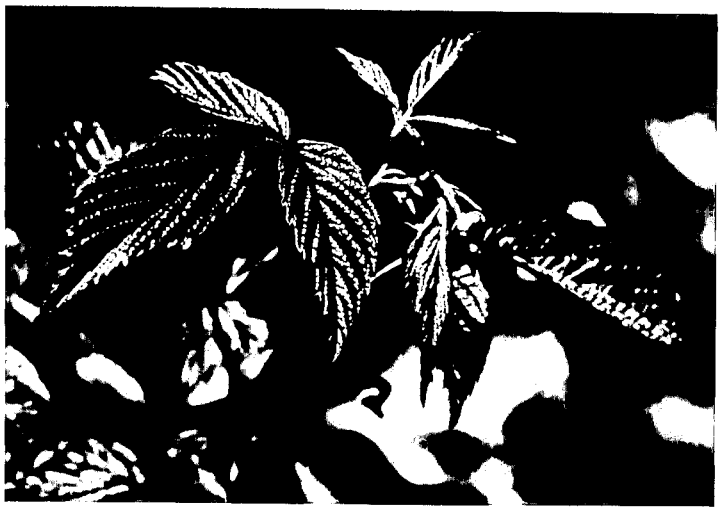
FIG. 4 illustrates typical immature leaves and the fruit stems with their typical purple discoloration which coloration extends to the base of the sepals when exposed to the sun.

The new variety herein designated "Stonehurst" has displayed outstanding novel characteristics such as (1) the everbearing fruiting habit, i.e., fruit is borne on primocanes during the first year after planting and during the second and subsequent years on primocanes and floricanes; (2) thornless canes, i.e., without prickles; (3) relative (as compared to Willamette and Sweetbriar) tolerance to the Pytophthera root rot species that attack raspberries in the Pajaro Valley of California; (4) exceptionally early cropping on both spring and fall crops; and, (5) high yields. On my farm in Watsonville, spring production on floricanes starts approximately May 1 and peaks during the last week of May and the first two weeks of June. Fall production on primocanes peaks from early August until mid-September. The spring crop generally comprises one third of the total crop and the fall crop two thirds. There is some production continuously from May until December. Cropping precedes that of the Willamette variety grown in the same field by approximately one month and yields throughout the course of the year exceed those of Willamette.

Plant Description: Terminology follows that of Asa Gray, Lessons in Botany, revised edition (1901). Everbearer, bearing on primocanes and floricanes; upright stiff canes reaching an average height by the second year after planting on my Watsonville farm of five to seven feet, which is about four feet shorter than the Willamette variety in the same field. Grown in hedgerows, the "Stonehurst" variety has a distinctly rounded appearance.

Primocanes are upright, rigid and non-branching, light green, lighter than the leaves, thornless, i.e., without prickles, except for slightly developed, soft reddish-brown prickles at the base, extending upward about one fifth the length of the cane. Floricanes are light brown and branching.

Foliage is mostly three-foliate with occasional five-foliate leaves. The terminal leaflet is cordate, occasionally developing single lobes or one lobe on each side situated approximately midway between the base and the apex. Lobe formation ranges from mere points to independent leaflets.

Mature leaves are cress green to dark cress green (see Plate XXXI, Color Standards and Color Nomenclature by Robert Ridgway, Washington, D.C. (1912)), rugose to corrugated, with valleys of corrugations traversed by veins. In general appearance, leaves bear a resemblance to those of Willamette. Immature leaves that were exposed to the sun show a marked purple coloration along the edges and on the ridges of corrugation. On small recently opened leaflets about ½ to ¾ inches long, the color is burnt lake (see Plate XII, Color Standards and Color Nomenclature by Robert Ridgway, Washington, D.C. 1912). As the leaflet matures, the purpling tends toward violet carmine (see Plate XII, Ridgway) and diminishes in area until it is gone altogether. The burnt lake coloration is also found on the pedicel and extends on to the base of the sepals on the side that is exposed to the sun.

Fruit is borne in raceme clusters, with the terminal cluster bearing six to twelve berries, and subterminal clusters, typically fewer. Fruit is partially hidden by foliage and picks easily. Fruit is rose red to pomegranate purple (see Plate XII, Ridgway). The berries are smaller than those of Willamette and larger than those of Heritage. Primary berries are composed of 95–105 drupelets. Fruit is generally round in shape, however, the surface appearance is irregular or rough as if some drupelets are compressed perhaps due to insufficient room on the receptacle for all drupelets to expand fully. Drupelets have a prominent median depression which is particularly evident on immature fruit.

The receptacle (torus) is cylindrical at its base where sepals are dry stamens remain attached, then tapers to a sharp point.

I claim:

1. The new and distinct variety of raspberry plant herein described and illustrated and identified by the characteristics enumerated above.

* * * * *